(12) United States Patent
Rodriguez Ciurana et al.

(10) Patent No.: US 10,507,086 B2
(45) Date of Patent: Dec. 17, 2019

(54) DENTAL PROSTHESIS WITH THREADED CROWN ON POST AND CORE

(71) Applicant: Sweden & Martina SpA, Due Carrare (IT)

(72) Inventors: Javier A. Rodriguez Ciurana, Barcelona (ES); Isabel Segala Torres, Barcelona (ES); Javier Vela Nebot, Barcelona (ES)

( * ) Notice: Subject to any disclaimer, the term of this patent is extended or adjusted under 35 U.S.C. 154(b) by 13 days.

(21) Appl. No.: 15/570,347

(22) PCT Filed: Apr. 7, 2016

(86) PCT No.: PCT/IB2016/051973
§ 371 (c)(1),
(2) Date: Oct. 29, 2017

(87) PCT Pub. No.: WO2016/189401
PCT Pub. Date: Dec. 1, 2016

(65) Prior Publication Data
US 2018/0140391 A1 May 24, 2018

(30) Foreign Application Priority Data
May 22, 2015 (ES) .................... 201530717

(51) Int. Cl.
*A61C 8/00* (2006.01)
*A61C 5/30* (2017.01)
*A61C 5/70* (2017.01)

(52) U.S. Cl.
CPC .............. *A61C 8/0054* (2013.01); *A61C 5/70* (2017.02); *A61C 8/0048* (2013.01); *A61C 8/0068* (2013.01); *A61C 8/0069* (2013.01); *A61C 8/0078* (2013.01); *A61C 5/30* (2017.02); *A61C 2008/0046* (2013.01)

(58) Field of Classification Search
CPC ... A61C 8/0054; A61C 8/0068; A61C 8/0069; A61C 5/70; A61C 5/30; A61C 2008/0046; A61C 13/225; F25B 43/00; F24F 13/28
(Continued)

(56) References Cited

U.S. PATENT DOCUMENTS 4,850,873 A * 7/1989 Lazzara ............... A61C 8/0048
433/173
5,281,140 A 1/1994 Niznick
(Continued)

FOREIGN PATENT DOCUMENTS

CN 203493758 3/2014
EP 0669111 A2 * 8/1995 ........... A61C 8/0048
(Continued)

OTHER PUBLICATIONS

KR 100788455 specification translation—https://worldwide.espacenet.com/publicationDetails/biblio?II=0&ND=3&adjacent=true&locale=en_EP&FT=D&date=20071224&CC=KR&NR=100788455B1&KC=B1#, retreived Jun. 10, 2018.*
WO 2014/091345 specification translation—https://worldwide.espacenet.com/publicationDetails/biblio?II=0&ND=3&adjacent=true&locale=en_EP&FT=D&date=20140619&CC=WO&NR=2014091345A2&KC=A2# retreived Jun. 10, 2018.*

*Primary Examiner* — Heidi M Eide
*Assistant Examiner* — Mirayda A Aponte
(74) *Attorney, Agent, or Firm* — Themis Law (57) ABSTRACT

A dental prosthesis with a threaded crown on a post and core includes a dental implant, a post and core having a portion adapted to be inserted into the implant and another portion protruding from the implant, a screw and a crown, the implant being adapted to be fixed to a bone and the post and core being adapted to be fixed to the implant with a thread, the crown being fixed to the post and core with the screw, wherein the post and core provides a connection element between the implant and the crown, a separation area being (Continued)

provided between the area where the post and core is housed in the crown and the area where the post and core is housed in the implant, and wherein the portion of the post and core protruding from the implant does not feature a diameter increase.

12 Claims, 6 Drawing Sheets

(58) Field of Classification Search
USPC .................................. 433/174–176, 201.1
See application file for complete search history.

(56) References Cited

U.S. PATENT DOCUMENTS

| | | | |
|---|---|---|---|
| 2006/0172257 A1* | 8/2006 | Niznick | A61C 8/0022 433/173 |
| 2006/0183078 A1* | 8/2006 | Niznick | A61C 8/0001 433/173 |
| 2008/0241789 A1 | 10/2008 | Mundorf | |
| 2011/0200969 A1 | 8/2011 | Schroering | |

FOREIGN PATENT DOCUMENTS

| | | | |
|---|---|---|---|
| FR | 2806291 | 9/2001 | |
| KR | 100788455 B1 * | 12/2007 | |
| WO | WO 2014091345 A2 * | 6/2014 | A61C 8/0025 |

* cited by examiner

DENTAL PROSTHESIS WITH THREADED CROWN ON POST AND CORE

The present invention concerns the dental sector, more particularly the sector of dental prostheses placed on implants. The present invention concerns, in particular, a dental prosthesis.

A prosthesis on implant consists in the placing of a dental prosthesis by means of an implant, for the purpose of obtaining a good aesthetic and functional result of the prosthesis or crown and of the tissues surrounding it. It is constituted by three functional parts: the implant, the post and core and the crown or prosthesis. Usually, each functional part corresponds to an independent element. The implant is introduced in the bone in order to provide a support for the post and core, which has the function of joining the implant with the crown. The post and core usually remains fixed to the implant by means of a thread and the crown can be joined to the post and core by means of a thread or through cementation. In the case of the prosthesis that is the subject of the present invention, the crown is preferably joined to the post and core through a threaded joining element.

The crowns placed on post and cores of the known type, both the cemented and the threaded ones, are designed in such a way that they rest on a margin or shoulder of the post and core. The margin is delimited within the post and core and consists of a supporting surface for the crown that is placed on the same. It constitutes a transition section between the diameter of the implant and the diameter of the crown and is located exactly at the level of the gum, so that the post and core is not visible. Since the gum healing process is rather slow, it is necessary to wait at least 3 months before being able to place the post and core definitively, as any slight recession would make the post and core visible and expose it to the bacteria present in the mouth.

The existence of a margin involves, on one hand, the impossibility to place the crown definitively at the same time as the implant and the need to wait for a long time before placing the crown definitively.

The healing of the gum around the post and core is of the type by secondary intention. This type of healing is characterized by a considerable contraction of the tissues due to myofibroblasts. The contraction of the tissues forces the gum to move towards a point in which the diameter of the post and core is smaller. The prostheses with margin or shoulder make it necessary for the profile of the post and core to diverge from the base. This forces the fibres of the tissue to stabilize at a lower level, with the risk of the post and core becoming exposed due to the fact that it has a smaller diameter.

Furthermore, all the prostheses (crowns) with margin or shoulder at least make it necessary to disconnect the post and core in order to place the final tooth with the defined margin. The disconnection of the post and core is the factor that causes the most accentuated gingival recession.

In standard post and cores, the diameter diverges from the highest point of the implant towards the lowest point of the crown, and therefore the smaller diameter is positioned at the base of the post and core, so that the gum tends to move towards the implant. This makes this type of post and cores less satisfying in terms of aesthetic appearance and also reduces their capacity to insulate the gum. If the insulation provided is not good, bacteria penetrate easily into the inner area, causing infections.

The tissue that remains in contact with the post and core in its area closest to the implant is called connective tissue. Post and cores have the function of holding the fibres of said connective tissue in order to stabilize the gum and insulate the implant from the contaminating environment of the mouth. For this purpose, the known post and cores are provided with a series of grooves in the area of the post and core that is closest to the implant. For example, the US patent US20110200969A1 describes a set of micro grooves that can be arranged with a certain inclination. However, the geometry of said micro grooves existing in the state of the art does not allow the regenerative capacity of the connective tissue to be fully exploited.

The prosthetic post and core incorporated in the dental prosthesis that is the subject of the present invention has the purpose to obtain better results than the known post and cores, in terms of both aesthetical appearance and biological functionality.

The present application practically describes a dental prosthesis with threaded crown on post and core, of the type comprising a dental implant, a post and core comprising a portion to be inserted into said implant and another portion protruding from said implant, a screw and a crown, said implant being suited to be fixed to a bone and said post and core being suited to be fixed to said implant by means of a thread, wherein the crown is fixed to said post and core by means of said screw, wherein said post and core serves as a connection element between said implant and said crown, and wherein a separation area or portion (identified with 5 in FIG. 2) is provided between the area where the crown is housed in the post and core and the area where the post and core is housed in the implant, said dental prosthesis being characterized in that the diameter of said portion of the post and core protruding from said implant shows no increase in diameter.

The present invention is not limited to cylindrical or conical shapes, meaning shapes with circular cross section. In the present application the word "diameter" must be understood widely, including the so-called hydraulic diameter or equivalent diameter for non-circular geometric shapes.

Optionally, said post and core comprises a hole provided with a thread and suited to accommodate said screw intended to fix the crown to the post and core. The post and core can be constituted by a single element, a solution that is mainly suitable for multiple replacements. The hole provided in the post and core allows the insertion of the screw that fixes the crown. The configuration of a post and core consisting of a single element is mainly suitable for multiple replacements, that is, for placing more than one prosthesis joined to one another.

Preferably, the post and core is constituted by an external hollow element and a through screw that is inserted into said hollow element and fixed to the implant, wherein said through screw comprises said hole with a thread housing said screw that fixes the crown to the post and core. The post and core can be constituted by two elements, an external hollow element and a through screw that is fixed to the implant and fixes also the external element. In this case, the hole suited to accommodate the screw that fixes the crown is located in the through screw. This configuration with the post and core divided in two elements is mainly suitable for single replacements, that is, for placing a single prosthesis.

Preferably, the diameter of said portion protruding from said implant converges in a continuous manner from said implant towards said crown, with no increase in diameter.

Optionally, the portion of the post and core that protrudes from said implant comprises one or more cylindrical segments longer than 0 mm and equal to or shorter than 3 mm extending from said implant towards the crown. More preferably, the portion of the post and core that protrudes from said implant comprises at least one cylindrical segment between 1 mm and 3 mm in length extending from said implant towards the crown, both limits included, and wherein said cylindrical segment is included between two conical segments.

In the preferred solution, the conical portion that is closer to the implant converges with an angle included between 6° and 15°, while the upper cone converges with an angle included between 2° and 6°.

According to an embodiment of the prosthesis according to the present invention, the diameter of said portion protruding from said implant converges in a continuous manner from the end of said cylindrical segment of the post and core towards the crown.

Preferably, the diameter of the post and core converges with an angle of convergence included between 1° and 8°. More preferably, the diameter converges with angles of convergence included between 2° and 5°.

During the first week, and part of the second, after the implant with the post and core has been placed the fibres increase in number. At the beginning, most of the fibres have a certain elasticity. The type of wound that is produced by perforating the gum is a wound healing by secondary intention. This means that starting from the second week part of the fibroblasts are transformed into myofibroblasts, which have the capacity to contract. Being arranged in a circular shape, and due to their tendency to contract, myofibroblasts tend to be positioned in the area of the post and core with smaller diameter. Thanks to the decrease in the diameter of the post and core, the area with smaller diameter is located at the limit of the crown, rather than in the implant as is the case with the known post and cores.

The fact that the diameter of the post and core decreases from the implant or from the end of the cylindrical segment towards the crown is not sufficient to ensure that the gum heals far from the implant. The crown can be positioned in the post and core in such a way that it is very near the implant and that the distance between the implant and the crown is very small or null. A crown with its lower part far from the highest part of the implant causes an accumulation of tissue further away from the implant. This ensures good insulation of the implant and a larger quantity of tissue, which improves the aesthetical appearance of the crown.

The fact that the converging inclination starts from the base is important, since tissues always regenerate starting from the innermost part, meaning the lowest part. In order for the above to take place, the base of the post and core must be positioned slightly under the surface, meaning that the implant must be inserted not too deep into the bone.

This improvement, furthermore, takes in consideration the possibility to improve the aesthetical result of a late gingival recession, as it is possible to change the crown of the prosthesis with no need to disconnect the post and core.

Preferably, said post and core has no margins. Since there is no need for margins, it is possible to place it at the same time as the implant and thus avoid any disconnection.

A unique characteristic that is typical of this post and core lies in that the crowns it supports can be different and the crown that rests on the margin of the post and core can have any margin. This factor facilitates the formation of a short joining piece of epithelium. This aspect is important, as one of the main differences with respect to the tissues that surround teeth and implants lies in that the epithelium of the implants is longer and has a higher tendency to recession. By using these post and cores, without disconnecting the prosthesis, it is possible to obtain a shorter piece of epithelium compared to the rest of the known prostheses, as well as a thicker and more stable connective tissue.

Preferably, said post and core is provided with a microscopic or micrometric ascending thread that starts from the part of said portion protruding from said implant that is closest to the implant itself. Optionally, the width of said microscopic thread is included between 4 µm and 100 µm, preferably it is equal to at least 20 µm. As a further option, the depth of said microscopic thread is included between 4 µm and 60 µm, preferably it is equal to at least 20 µm.

The fibres of connective tissue (1-20 microns in diameter) start to surround the post and core according to a circular pattern, as the post and core is circular. Said fibres are produced by the fibroblasts. The maximum diameter of a fibre (20 microns) will determine the minimum depth and width of the micro threads.

The tissues always regenerate starting from the deepest part and moving towards the surface. The presence of a continuous thread facilitates the movement of the fibres from the deepest part of the post and core to the most exposed area of the same. The size of the thread is smaller than that known in the art. This means that there will be less space for the proliferation of bacteria. Also the depth is reduced, and therefore the vasa of the connective tissue are able to fight against infections.

In any case, it is the epithelium that has the function of physically stopping the passage of bacteria, and this is at a further level, thanks to the type of crown on implant that is produced without margins and in a specific manner.

In the prosthetic post and cores known in the art, the micro grooves have the capacity to stabilize collagen fibres so that they seem to be directly fixed into them. However, the inventors hereof have found that the fibres are arranged so as to form a ring and remain fixed within the grooves of the threads.

In order for the reader to better understand the invention, an example of embodiment of the same is described here below by way of non-limiting example, with reference to some drawings.

Figure 1:
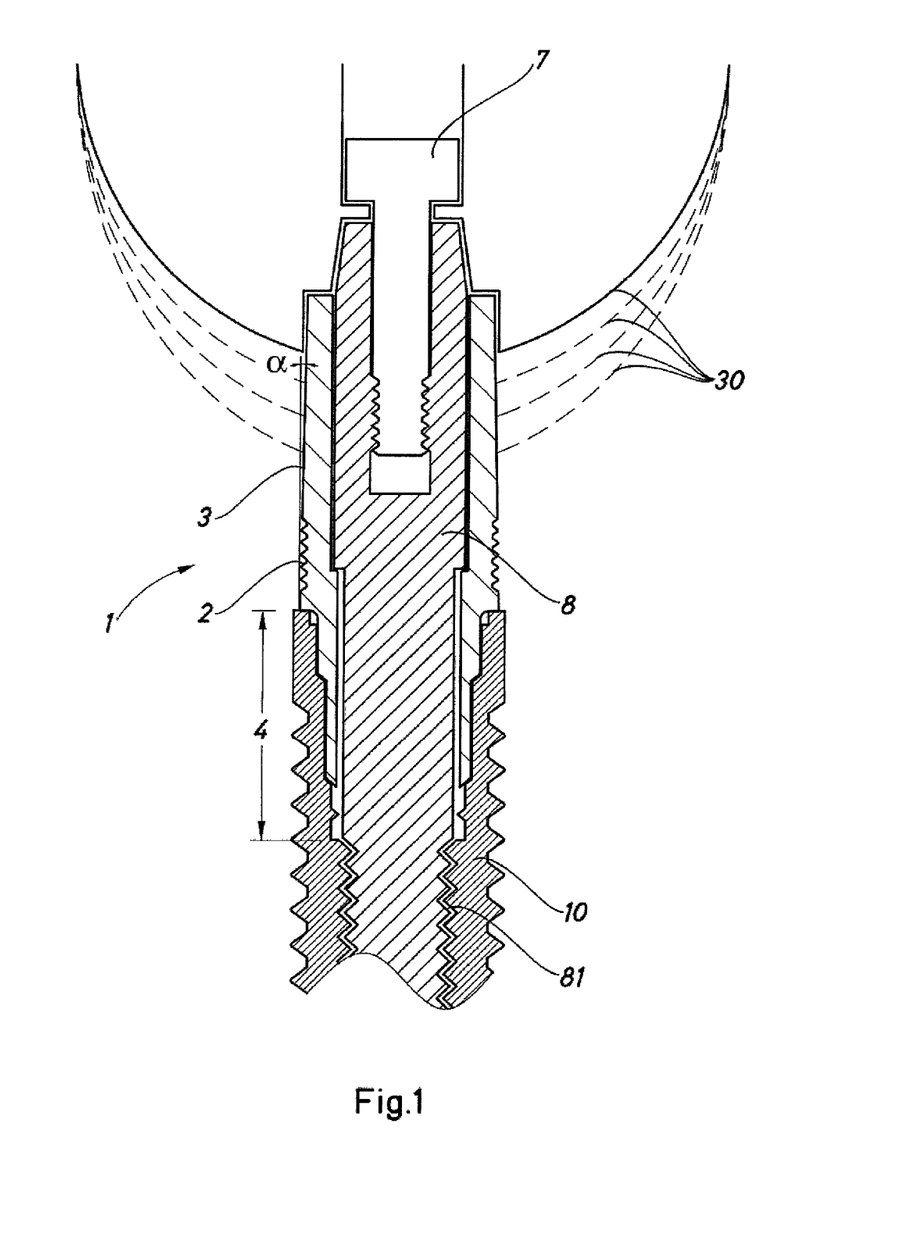
FIG. 1 shows a sectional view of an embodiment of a prosthetic post and core according to the present invention.

The prosthetic post and core 1 shown in FIG. 1 is hollow and is internally provided with an area that extends in the direction of its axis of symmetry, thus allowing the insertion of a through screw 8. Said through screw 8 remains fixed inside the post and core 1 and its male thread 81 is joined to the female thread of the implant 10. The portion of the post and core 1 that is inserted in the implant 10 is called connecting portion 4 and corresponds to an area of the post and core 1 with smaller diameter.

The through screw 8 comprises in its top part, that is, the part closest to the crown 30, a hole provided with a female thread for the insertion of a screw 7 that allows the crown 30 to be fixed to the post and core 1. This type of fixing makes it possible to position the crown 30 at different heights in order to be able to adapt the position to the specific characteristics of each individual gum. The broken lines indicated by 30 show possible positions of the crown 30.

On the other hand, the diameter of the post and core 1 shown in FIG. 1 converges upwards for the entire portion protruding from the implant, that is, starting from the connecting portion 4. The angle of convergence α is included between 2° and 5°. In the part closest to the connecting portion, the post and core 1 is provided with an ascending micrometric thread 2 that starts after the connecting portion 4.

Figure 2:
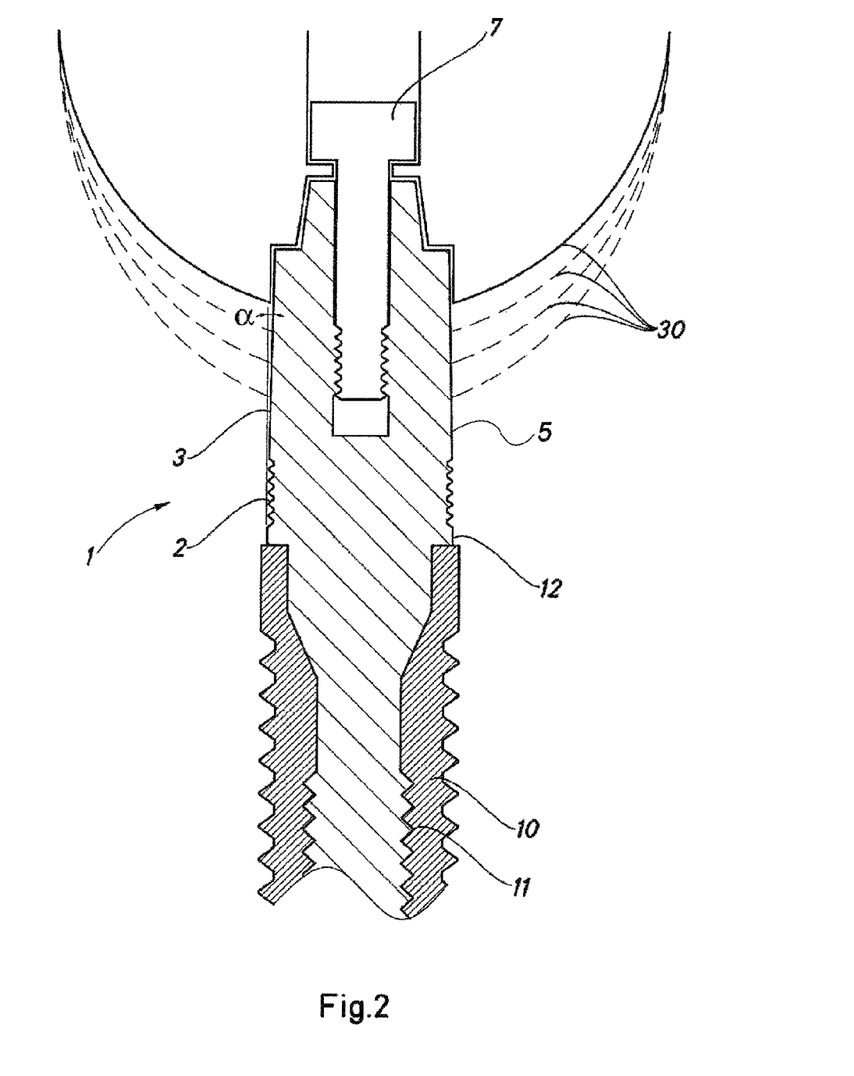
FIG. 2 shows a sectional view of a second embodiment of a prosthetic post and core according to the present invention.

The prosthetic post and core 1 according to the present invention can be carried out without the through screw 8, as in the embodiment shown in FIG. 2. In this case, the post and core 1 is joined to the implant 10 thanks to the thread 11 that is provided in its lower part, while in its upper part, meaning the part closest to the crown 30, has a hole with a female thread for the insertion of the screw 7. The typical post and core 1 has the characteristics that are necessary to fix it to the implant 10 and to house the screw 7 that allows the crown 30 to be joined to the post and core 1.

The prosthetic post and core of the embodiment shown in FIG. 2, furthermore, is fixed in such a way that it allows the crown 30 to be positioned at different heights in order to adapt its position to the specific characteristics of each individual gum. The broken lines indicated by 30 show possible positions of the crown 30.

The post and core 1 with through screw 8 of the embodiment shown in FIG. 1 is mainly suitable for single replacements, that is, when just one implant needs to be placed. On the other hand, the prosthetic post and core 1 without through screw of the embodiment shown in FIG. 2 is mainly used for multiple replacements, that is, in the cases where several prostheses joined to one another need to be placed.

It is also possible to observe in FIG. 2 that the portion of the post and core 1 protruding from the implant 10 has a cylindrical segment 12 that is longer than 0 mm and equal to or shorter than 3 mm. This characteristic can be applied to any embodiment of the dental prosthesis according to the present invention. In this alternative embodiment, the convergence of the diameter of the post and core 1 starts at the end of the cylindrical segment 12. The angle of convergence α is included between 2° and 5°. In its area closest to the implant, the post and core 1 is provided with an ascending micrometric thread 2 that starts immediately after the cylindrical segment 12.

Figure 3:
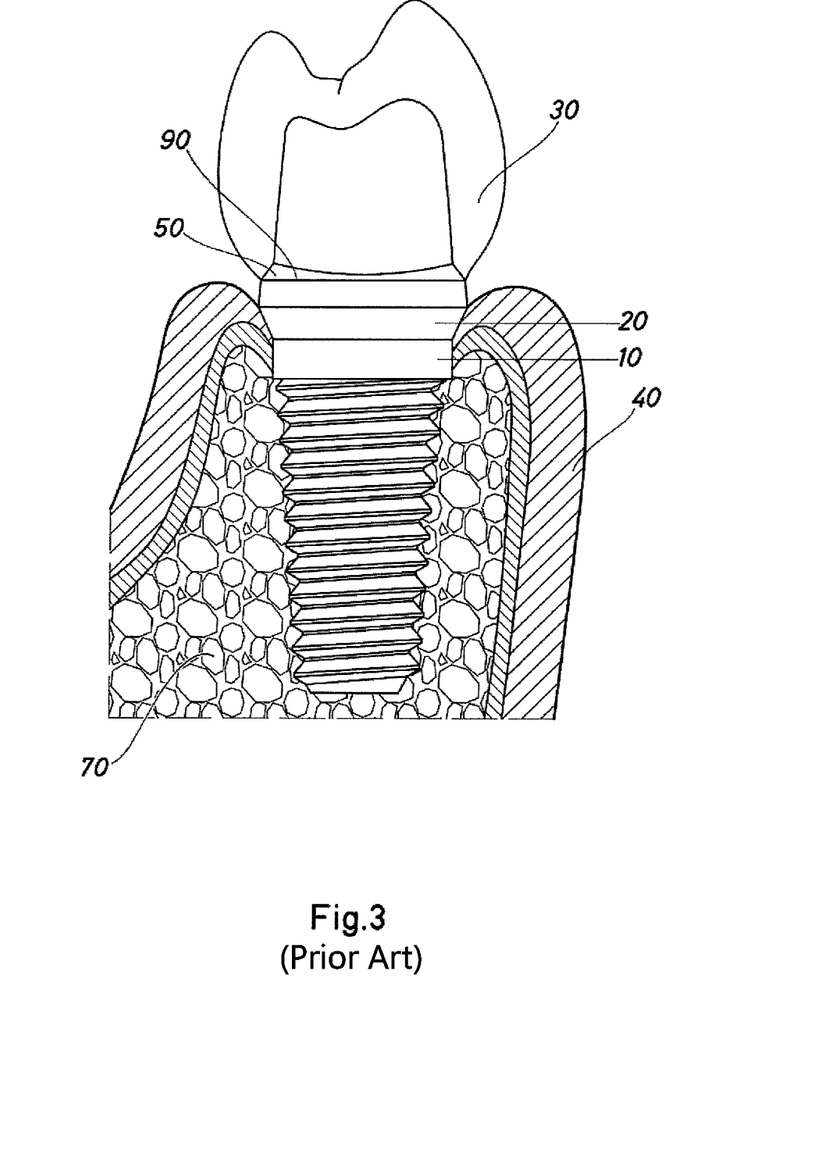
FIG. 3 shows a front view of a dental prosthesis with a post and core of the known type with margin or shoulder.

A typical post and core known in the art has a margin or shoulder such as, for example, that indicated by the numeral 50 in FIG. 3. The presence of the margin 50 implies that the diameter of the post and core 20 increases immediately after the implant 10, thus defining the margin or shoulder 50. The crown 30 has a part that comes to be fixed into the margin 50 of the post and core 20 and rests on the same, leaving the base of the crown 30 at the same level as the supporting line 90.

Figure 2B:
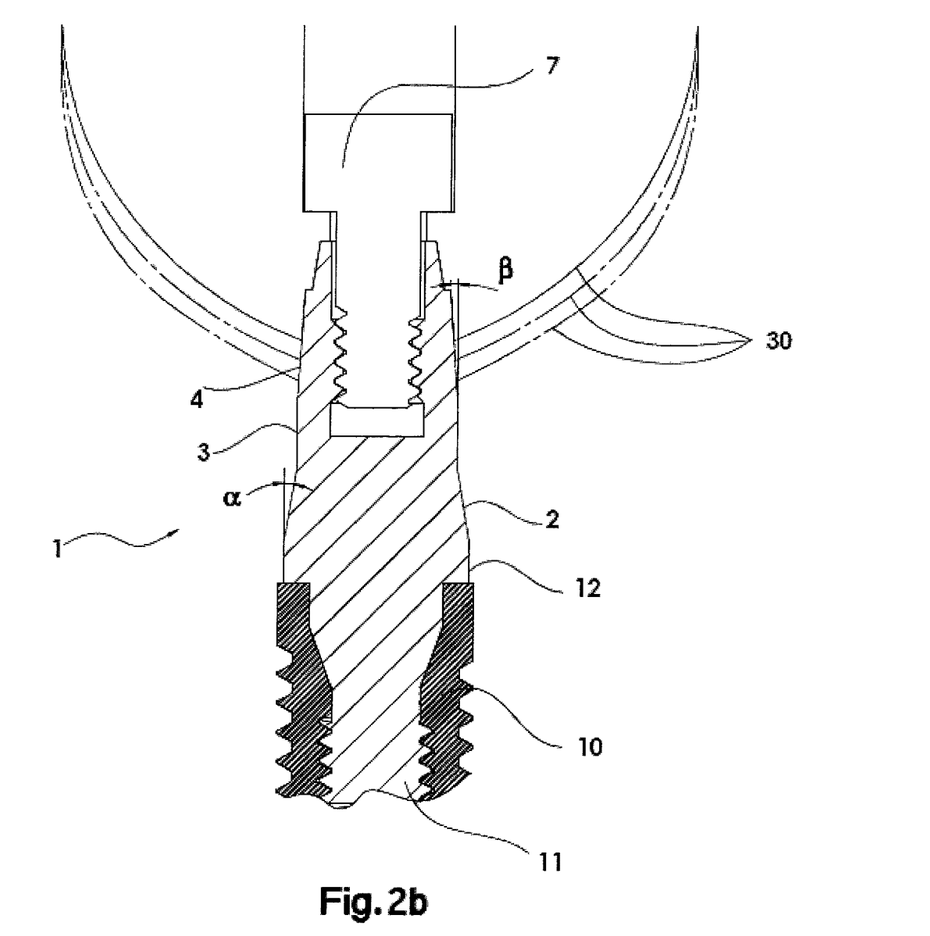
FIG. 2b shows a sectional view of a variant of the second embodiment of the prosthetic post and core according to the present invention.

FIG. 2b shows a variant in which the cylindrical portion 3 is included between two conical portions 2 and 4.

In the known post and cores like the one shown in FIG. 3, the narrowest area of the post and core 20, in the part located between the implant 10 and the crown 30, is exactly in the contact point between the post and core 20 and the implant 10. This causes the healed tissue to accumulate in this area and leads to the recession of the gum 40 that exposes the post and core 20, as can be seen in FIG. 3, thus negatively affecting the aesthetical appearance of the implant and exposing the gum to the proliferation of bacteria.

Figure 4:
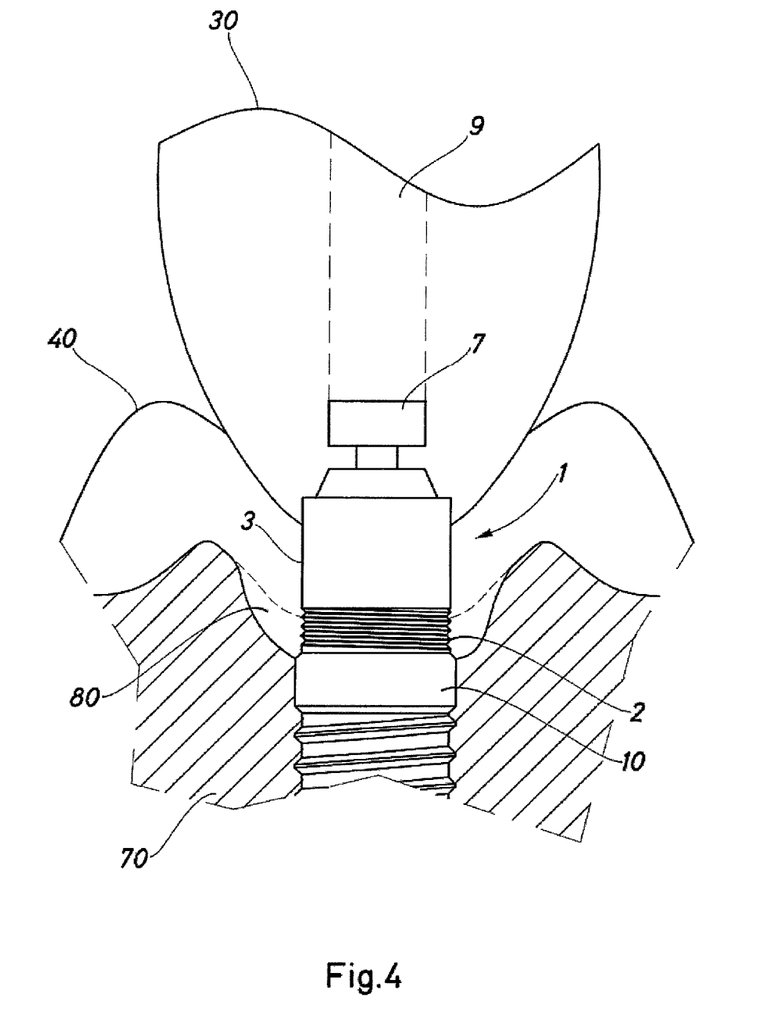
FIG. 4 shows a front view of the post and core of FIG. 1 fixed to an implant inserted in a bone and having a crown placed on it, wherein the contour of the post and core is highlighted with respect to the other elements so as to show its position within the crown.

FIG. 4 shows the prosthetic post and core 1 that is the subject of the present invention joined to an implant 10 fixed to a bone 70, and with a crown 30 on the same. The area of interest corresponds to the part of the post and core 1 that is situated between the implant 10 and the crown 30. In FIG. 4 the contour of the post and core 1 is highlighted in order to show its position within the crown 30. As can be observed, from the area of the post and core exposed to contact with the gum 40, the smaller diameter is exactly at the limit between the post and core 1 and the crown 30.

Figure 5:
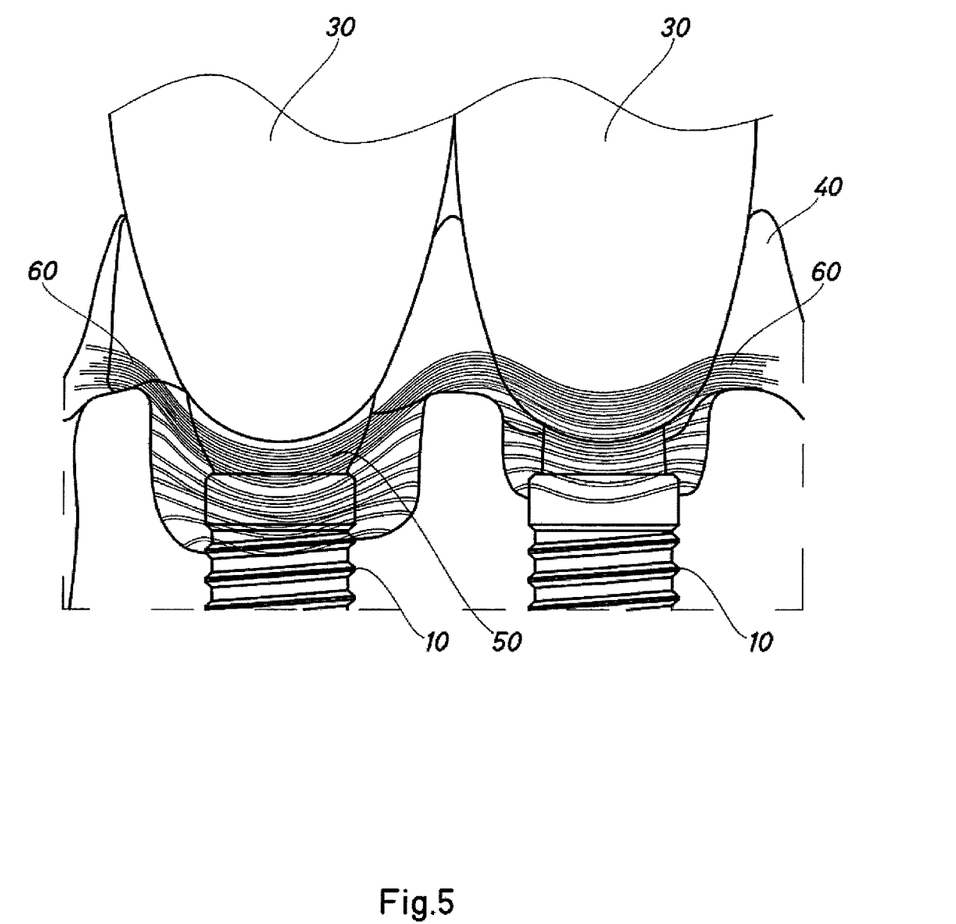
FIG. 5 shows a front view of two dental prostheses. The left prosthesis corresponds to a known post and core with margin or shoulder and the right prosthesis corresponds to a prosthetic post and core according to the present invention, illustrated schematically (the micro thread is not shown).

This causes the gum 40 to accumulate in the lower part of the crown 30 during the healing process and consequently, due to the separation of said lower part of the crown 30 from the implant 10, the quantity of tissue between the crown and the implant is larger than in the known post and cores, as shown in FIG. 5.

FIG. 4 shows how the gum 40 covers the post and core 1 completely, differently from that which happens with the post and cores known in the art, as that shown in FIG. 3. The numeral 80 indicates the portion of tissue that is fixed to the micrometric thread 2.

In order to allow the fixing operation to be performed between the post and core 1 and the crown 30 through the threaded joining element, the crown 30 is provided with a hole 9 that allows access to the head of the screw 8. Once the joining operation has been completed, the hole 9 is filled with a resin-based material in order to seal the cavity and prevent the introduction or release of bacteria and give a better appearance to the crown 30.

The left dental prosthesis in FIG. 5 uses a post and core with margin or shoulder 50 like those known in the art. The gum 40 covers a smaller part of the crown 30 and is closer to the implant compared to the prosthesis with the prosthetic post and core that is the subject of the present invention, shown on the right. The effect thanks to which the area with smaller diameter is further from the implant allows a larger quantity of tissue to be present between the implant 10 and the crown 30. This can be observed from the different position of the tissue fibres 60 in the two prostheses. In the case of the known post and core with margin (on the left), the fibres 60 are located in an area closer to the implant and with little contact with the post and core. On the contrary, in the case of the post and core according to the present invention (on the right), the fibres 60 adhere to the entire surface of the post and core and in an area closer to the crown, with more tissue between the crown and the implant compared to the prosthesis illustrated on the left.

Even though the invention has been described with reference to a preferred example of embodiment, this is not to be intended as a limiting condition, the invention being defined by the following claims.

The invention claimed is:

1. A dental prosthesis comprising:
   a dental implant;
   a post and core comprising a first portion adapted to be inserted into said implant and a second portion protruding from said implant;
   a screw; and
   a crown, said implant being adapted to be fixed to a bone and said post and core being adapted to be fixed to said implant through a thread, wherein said crown is fixed to said post and core with said screw, wherein said post and core operates as a connection element between said implant and said crown, wherein said second portion comprises a separation portion between an apical end of the crown when the post and core is housed in the crown and a coronal end of the implant when the post and core is housed in the implant, wherein said separation portion of the post and core has a decreasing diameter in a coronal direction of the post and core, wherein said post and core comprises a first element and a second element, the first element being hollow and the second element comprising a through screw that is inserted in said first element and is fixed to the implant, said through screw comprising a hole provided with a thread suited to accommodate said screw that fixes the crown to the post and core, and wherein the second portion of the post and core that protrudes from said implant comprises one or more cylindrical segments having a length up to 3 mm and extending in the coronal direction.

2. The dental prosthesis according to claim 1, wherein the decreasing diameter of said separation portion of the post and core protruding from said implant has a frusto-conical shape in the coronal direction from an end of one of the one or more cylindrical segments of the post and core.

3. The dental prosthesis according to claim 2, wherein the frusto-conical shape has lateral wall with an angle of convergence in relation to a longitudinal axis included between 1° and 8°.

4. The dental prosthesis according to claim 3, wherein the angle of convergence is included between 2° and 5°.

5. A dental prosthesis comprising:
a dental implant
a post and core comprising a first portion adapted to be inserted into said implant and a second portion protruding from said implant;
a screw; and
a crown,
said implant being adapted to be fixed to a bone and said post and core being adapted to be fixed to said implant through a thread, wherein said crown is fixed to said post and core with said screw, wherein said post and core operates as a connection element between said implant and said crown, wherein said second portion comprises a separation portion between an apical end of the crown when the post and core is housed in the crown and a coronal end of the implant when the post and core is housed in the implant, wherein said separation portion of the post and core has a decreasing diameter in a coronal direction of the post and core, and wherein said separation portion of said post and core is provided, on an external surface thereof protruding from the implant, with an ascending microscopic thread that starts in proximity to the implant.

6. The dental prosthesis according to claim 5, wherein the decreasing diameter of said separation portion of the post and core causes said separation portion to have a frusto-conical shape.

7. The dental prosthesis according to claim 6, wherein the decreasing diameter converges with an angle of convergence included between 1° and 8°.

8. The dental prosthesis according to claim 5, wherein said post and core is made as a one piece structure.

9. The dental prosthesis according to claim 5, wherein a width of said microscopic thread is included between 4 μm and 100 μm.

10. The dental prosthesis according to claim 9, wherein the width of said microscopic thread is at least equal to 20 μm.

11. The dental prosthesis according to claim 5, wherein a depth between root and crest of said microscopic thread is between 4 μm and 60 μm.

12. The dental prosthesis according to claim 11, wherein the depth between root and crest of said microscopic thread is at least equal to 20 μm.

* * * * *